United States Patent [19]

Klehm

[11] Plant 4,234

[45] Apr. 4, 1978

[54] PEONY NAMED WHOPPER

[75] Inventor: Roy G. Klehm, Barrington, Ill.

[73] Assignee: Klehm Boys' Partnership, Arlington Heights, Ill.

[21] Appl. No.: 787,715

[22] Filed: Apr. 14, 1977

[51] Int. Cl.[2] ..... A01H 5/00

[52] U.S. Cl. ..... Plt./68

[58] Field of Search ..... Plt./68

*Primary Examiner*—Robert E. Bagwill

[57] ABSTRACT

A new variety of peony plant characterized by the very large size of its flamboyant flowers which are distinguished by large, notched and slightly ruffled guard petals, and by a pleasing soft pink overall coloring. This new plant is also characterized by its profuse, midseason production of fragrant flowers having an above average lasting quality both on the plant and as a cut flower.

1 Drawing Figure

ORIGIN OF THE NEW PLANT

This new peony plant originated as a seedling of Charlies White (P.P. 3,684) × Alice Harding (unpatented) and was discovered by applicant at his nursery gardens in Arlington Heights, Ill., the said cross having been made in the course of a breeding program carried on at Arlington Heights, Ill., with the object of producing improved garden peonies having strong, stiff stems and reliable weather resistant blossoms, as well as new flower colors and shapes.

This new plant was reproduced by applicant at Arlington Heights, Ill., by means of root division, and subsequent propagation, by the same method through successive generations, has demonstrated that the novel and distinctive features hold true and appear to be firmly fixed.

This new variety of peony plant is now being grown for the commercial market at production grounds at Arlington Heights, Ill., and at Champaign, Ill., propagation on a large scale being done by root division.

DESCRIPTION OF THE DRAWING

This new peony plant is illustrated by the accompanying photographic drawing which shows, in full color, the flower form of the blossom in full bloom, the soft pink color shown being as nearly true to nature as is reasonably possible to obtain by conventional photographic procedures.

DESCRIPTION OF THE NEW PLANT

The following is a detailed description of this new peony plant variety with color specifications according to the R.H.S. Colour Chart published by The Royal Horticultural Society at London, England, the observations having been made at Arlington Heights, Ill.

THE PLANT

Origin: Seedling.
Parentage:
*Seed parent.*—Charlies White (P.P. 3,684).
*Pollen parent.*—Alice Harding (unpatented).
Classification: *Paeonia lactiflora.*
Form: Bush.
Height: 34 to 35 inches.
Growth: Herbaceous, with average growth rate, sturdy and upright, with above average strength.
*Stem size.* —½ to 9/16 inch in diameter.

Foliage: Quantity — abundant.
*Leaf size.*—Large.
*Leaf shape.*—Elliptically acute with smooth margins.
*Aspect.*—Glossy.
*Color.*—Upper side—Forest Green 135A.
Under side—Almond Green 135B.

THE BUD

Size: Large.
*Diameter.*—1⅜ inch.
*Depth.*—1½ inch.
Form: Ellipsoidal and smooth.
Opening rate: Average.
Color:
*When sepals first divide.*—36B.
*When sepals begin to unfurl.*—36C.
Sepals: Hooded over bud until dividing; curl back as bud opens.
*Color.*—Green.
Calyx: Shape — Polysepalous.
*Splitting.*—Calyx does not split.
*Aspect.*—Smooth.

THE FLOWER

Blooming habit: The plant blooms profusely, once each year, in late May to early June.
Borne: Generally as a cluster with one terminal flower and three or four laterals.
Size: Very large.
*Diameter.*—7 to 8½ inches.
*Depth.*—3 to 3½ inches.
Shape: Cup-shaped when bloom first opens, becoming a fully classic bomb type of flower as the bloom matures and the guard petals fall outwardly to form a generally radial collar.
Petalage: Extremely double.
*Arrangement.*—Compact bomb shape central cluster with imbricated guard petals.
*Form.*—Spatulate with slightly serrated and ruffled margin.
*Color.*—Both sides of all petals — Orient Pink 35C-D.
*Texture.*—Soft.
*Appearance.*—Satiny.
Fragrance: Mild peony.

Disease resistance: Relatively healthy resistance to normal peony diseases, as observed at Arlington Heights, Ill., and at Springfield, Ill.

Persistence: Petals fall off the stem.

Lasting quality.

*On the plant.*—Above average.

*As cut flower.*—Above average.

REPRODUCTIVE ORGANS

Stamens: None.

Pistils: three in number.

*Length.*—$\frac{3}{4}$ inch.

*Stigmas.*—Color — Light Green

The individual flowers of this new peony variety are believed to be the largest of any bomb type of flower. The flower color is a pleasing soft pink for all of its petals and the ruffled margins of its broad, slightly curved guard petals surrounding the central ball of petals provide a flamboyant and carefree aspect.

I claim:

1. A new and distinct variety of peony plant substantially as herein shown and described, distinguished by the very large size of its soft pink bomb type flowers borne on sturdy stiff stems, its late spring blooming habit and by the above average lasting quality of the flowers.

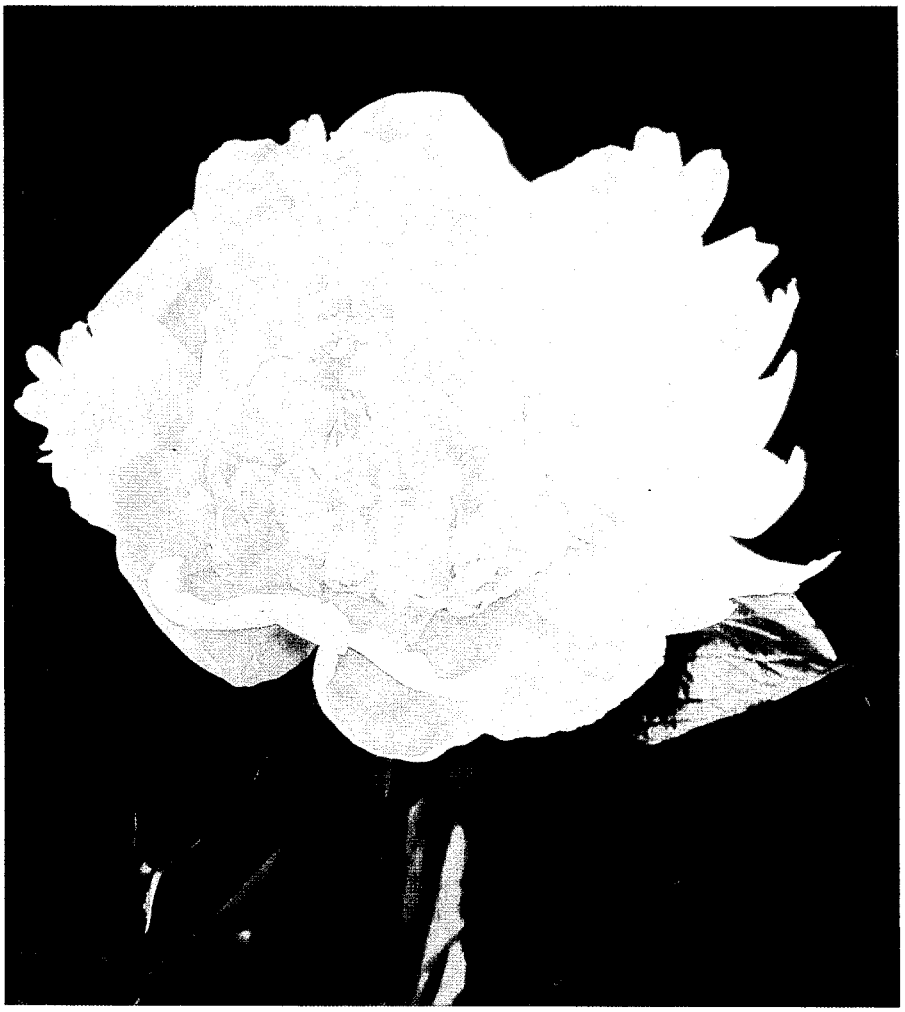

* * * * *